US011207300B2

United States Patent
Cipolli et al.

(10) Patent No.: US 11,207,300 B2
(45) Date of Patent: Dec. 28, 2021

(54) METHOD OF TREATMENT OF SHWACHMAN-DIAMOND SYNDROME

(71) Applicant: Marco Cipolli, Verona (IT)

(72) Inventors: Marco Cipolli, Verona (IT); Valentino Bezzerri, Verona (IT); Baroukh Maurice Assael, Milan (IT)

(73) Assignee: Marco Cipolli

( * ) Notice: Subject to any disclaimer, the term of this patent is extended or adjusted under 35 U.S.C. 154(b) by 0 days.

(21) Appl. No.: 16/332,913

(22) PCT Filed: Sep. 13, 2017

(86) PCT No.: PCT/EP2017/073042
§ 371 (c)(1),
(2) Date: Mar. 13, 2019

(87) PCT Pub. No.: WO2018/050706
PCT Pub. Date: Mar. 22, 2018

(65) Prior Publication Data
US 2019/0231753 A1    Aug. 1, 2019

Related U.S. Application Data

(60) Provisional application No. 62/393,747, filed on Sep. 13, 2016.

(51) Int. Cl.
| | | |
|---|---|---|
| *A61K 31/4245* | (2006.01) |
| *A61P 19/08* | (2006.01) |
| *A61P 1/18* | (2006.01) |
| *A61P 7/06* | (2006.01) |
| *A61P 43/00* | (2006.01) |

(52) U.S. Cl.
CPC ............ *A61K 31/4245* (2013.01); *A61P 1/18* (2018.01); *A61P 7/06* (2018.01); *A61P 19/08* (2018.01); *A61P 43/00* (2018.01)

(58) Field of Classification Search
CPC ............................ A61K 31/4245; A61P 19/00
USPC ......................................................... 514/364
See application file for complete search history.

(56) References Cited

U.S. PATENT DOCUMENTS

2016/0199357 A1 *   7/2016   Almstead ................ A61P 11/00
                                                        514/364

FOREIGN PATENT DOCUMENTS

| WO | 2006/110483 A1 | 10/2006 | |
| WO | 2008/039431 A2 | 4/2008 | |
| WO | WO-2008039431 A2 * | 4/2008 | ......... A61K 31/4245 |
| WO | 2012/016930 A1 | 2/2012 | |
| WO | 2015/035091 A1 | 3/2015 | |

OTHER PUBLICATIONS

International Search Report and Written Opinion of the International Searching Authority, PCT/EP2017/073042, European Patent Office, dated Nov. 22, 2017.

* cited by examiner

*Primary Examiner* — Craig D Ricci
*Assistant Examiner* — Janet L Coppins
(74) *Attorney, Agent, or Firm* — Valauskas Corder LLC

(57) ABSTRACT

The invention relates to compounds for the treatment of ribosomopathies. In particular, it refers to compounds for the treatment of Shwachman-Diamond Syndrome (SDS) and other ribosomopathies, such as Diamond-Blackfan Anemia (DBA), X-linked dyskeratosiscongenita (DKC) and Treacher Collins syndrome (TCS).

13 Claims, 8 Drawing Sheets

METHOD OF TREATMENT OF SHWACHMAN-DIAMOND SYNDROME

FIELD OF THE INVENTION

Figure 1:
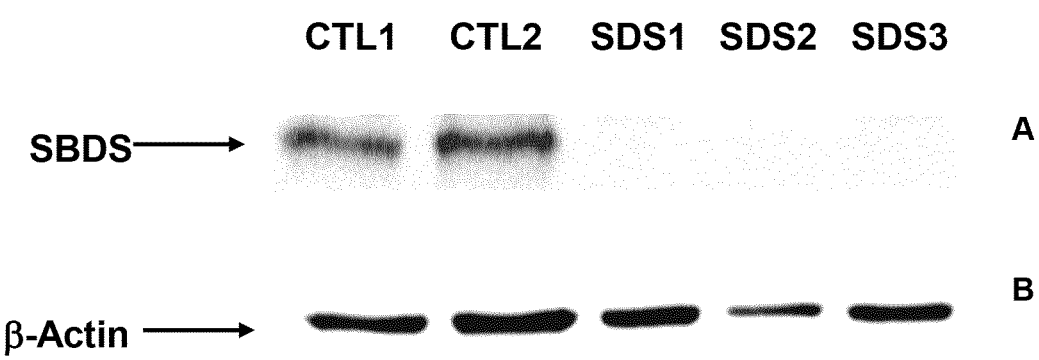

The invention relates to premature stop codons read-through drugs for the treatment of ribosomopathies. In particular, it refers to premature stop codons read-through drugs for the treatment of Shwachman-Diamond Syndrome (SDS) and other ribosomopathies, such as Diamond-Blackfan Anemia (DBA), X-linked dyskeratosis congenita (DKC) and Treacher Collins syndrome (TCS). Indeed, these diseases display similar phenotypes such as bone marrow failure, impaired hematopoiesis and bone defects. Furthermore, SDS, DBA and DKC are associated to myelodysplasia (MDS) and acute myeloid leukemia (AML).

BACKGROUND

Ribosomopathies are a heterogeneous class of diseases caused by alterations in ribosomal components, or in ribosomal structure and function[1]. Clinical features of the ribosomopathies, including Shwachman-Diamond Syndrome (SDS), Diamond-Blackfan Anemia (DBA), X-linked dyskeratosis congenita (DKC) and Treacher Collins syndrome (TCS), are bone marrow failure, hematological impairment, developmental abnormalities and increased risk of cancer[1].

Shwachman-Diamond Syndrome (SDS) is an autosomal recessive disease caused by mutations affecting the Shwachman-Bodian-Diamond syndrome (SBDS) gene[2], which encodes for the SBDS protein. It has been reported that human SBDS protein is enriched in nucleolus and it seems to be associated with the ribosomal RNA (rRNA) biogenesis[4]. Consistently with this observation, it has recently been postulated that SBDS plays a role during the maturation of the pre-60S ribosomal subunit, allowing the formation of the 80S ribosome[5]. However, the exact function of SBDS protein and its role in SDS is still unknown.

SDS has a prevalence of 1-9/1,000,000; it affects 1/168,000 newborns in Italy with a mean of 3.0 new cases/year[3]. Compound heterozygous mutations of the SBDS gene on chromosome 7 are present in the majority of patients with SDS. Most of these mutations resulted from gene conversion with a neighboring pseudogene (SBDSP). Based on the Italian Shwachman-Diamond syndrome registry, most of SDS patients (58%) present nonsense mutations at least in one allele of SBDS gene, similarly to data obtained in a Canadian cohort of 158 families[2].

Supportive care, pancreatic enzyme replacement, G-CSF for severe neutropenia, and matched sibling stem cell transplantation are currently the standards of care for SDS. However, no treatment able to cure SDS defects has been developed so far.

SDS pathology is characterized by a multiple-organ impairment involving bone marrow dysfunctions, exocrine pancreatic insufficiency, skeletal malformations, hepatic and cognitive disorders[7]. SDS patients present severe hematologic disorders, in particular neutropenia and impaired neutrophil chemotaxis that contribute to recurrent infections in young children[8].

Notably, SDS patients have also an increased propensity for bone marrow failure (about 15% of the cases) and leukemia; in particular, acute myeloid leukaemia (AML) is described in 11% of the SDS patients present in the French Severe Chronic Neutropenia Registry[9]. The progression through AML has been hypothesized as a pro-leukemic effect of SBDS mutations, which promotes karyotype instability that in turn leads to clonal anomalies in bone marrow cells[10].

Other ribosomopathies include Diamond-Blackfan Anemia that can be caused by mutations in the RPL5, RPL11, RPL35A, RPS7, RPS10, RPS17, RPS19, RPS24, and RPS26 genes, inherited in an autosomal dominant pattern. These genes provide instructions for making several of the approximately 80 different ribosomal proteins, which are components of cellular structures called ribosomes. In Diamond-Blackfan anemia, the bone marrow malfunctions and it fails to make enough red blood cells, which carry oxygen to the body's tissues. The resulting shortage of red blood cells (anemia) usually becomes apparent during the first year of life. Symptoms of anemia include fatigue, weakness, and an abnormally pale appearance (pallor). Dyskeratosis congenita is classically defined by the triad of abnormal skin pigmentation, nail dystrophy, and leukoplakia of the oral mucosa. Progressive bone marrow failure occurs in over 80% of cases and is the main cause of early mortality. The phenotype is highly variable, and affected individuals may have multiple additional features, including pulmonary fibrosis, liver cirrhosis, premature hair loss and/or graying, osteoporosis, atresia of the lacrimal ducts, and learning difficulties. Predisposition to malignancy is an important feature.

Treacher Collins syndrome is a condition that affects the development of bones and other tissues of the face. The signs and symptoms of this disorder vary greatly, ranging from almost unnoticeable to severe. Association with Diamond-Blackfan anemia has been reported.

In the aim of providing a treatment for ribosomopathies in general, and in particular for SDS, it is thus extremely important to provide a treatment that is capable of ameliorating the bone marrow functionality.

WO2004091502 describes small molecules capable of suppressing premature translation termination by mediating the misreading of the nonsense codon, among them Ataluren (PTC124), {3-[5-(2-fluorophenyl)-[1,2,4]oxadiazol-3-yl]-benzoic acid}. Ataluren is a small molecule that demonstrated dose-dependent read-through of premature stop codons (PTCs) generated by nonsense mutations[11]. Low concentrations (0.01-10 μM) of Ataluren promote significant PTC suppression in tissue culture and it has been preclinically tested in several models of nonsense-mediated diseases, including cystic fibrosis (CF), Miyoshy myopathy, Hurler syndrome, Usher syndrome and Batten disease[12]. However, results are contrasting so far. As an example, no statistically significant improvement in lung function or exacerbation rate in the population of cystic fibrosis patients with nonsense mutations treated with Ataluren has been observed[13].

SUMMARY OF THE INVENTION

The inventors have surprisingly found that compound of formula (I)

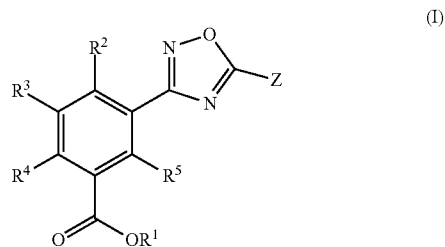

wherein Z is substituted or unsubstituted aryl, substituted or unsubstituted heteroaryl, substituted or unsubstituted cycloalkyl, substituted or unsubstituted alkyl, substituted or unsubstituted alkenyl, substituted or unsubstituted heterocycle, substituted or unsubstituted arylalkyl;

$R^1$ is hydrogen, substituted or unsubstituted alkyl, substituted or unsubstituted cycloalkyl, substituted or unsubstituted heterocycloalkyl, substituted or unsubstituted aryl, substituted or unsubstituted heteroaryl, —(CH$_2$CH$_2$)$_n$OR$^6$ or any biohydrolyzable group;

$R^2$, $R^3$, $R^4$, $R^5$ and $R^6$ are independently hydrogen, substituted or unsubstituted alkyl, substituted or unsubstituted alkenyl, substituted or unsubstituted alkynyl; substituted or unsubstituted cycloalkyl, substituted or unsubstituted heterocycloalkyl, substituted or unsubstituted aryl, substituted or unsubstituted heteroaryl, alkoxy, aryloxy, heteroaryloxy, halogen, CF$_3$, OCF$_3$, OCHF$_2$, CN, COOH, COOR$_7$, SO$_2$R$^7$, NO$_2$, NH$_2$, or N(R$^7$)$_2$;

each occurrence of $R^7$ is independently hydrogen, substituted or unsubstituted alkyl, substituted or unsubstituted alkenyl, substituted or unsubstituted alkynyl; substituted or unsubstituted cycloalkyl, substituted or unsubstituted heterocycloalkyl, substituted or unsubstituted aryl, substituted or unsubstituted heteroaryl, alkoxy, aryloxy, heteroaryloxy, halogen or CF$_3$; and n is an integer from 1 to 7;

or a compound of formula (II)

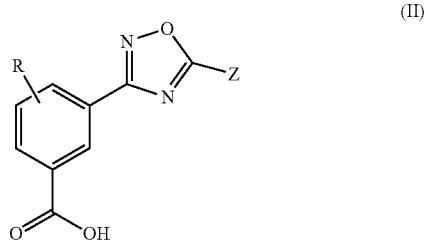

wherein Z is defined as in formula I and R is hydrogen or halogen are capable to rescue the ribosomopathy phenotype. In particular, the compounds are useful in ameliorating hematopoietic cells dysfunctions associated with SDS ribosomopathy.

FIGURES

FIG. 1. SBDS and β-actin protein expression in LCLs obtained from B cells from healthy donor subjects (CTL1 And CTL2) and from SDS patients (SDS1-3) carrying both the 258+2T>C and 183-184TA>CT mutations.

Figure 2:
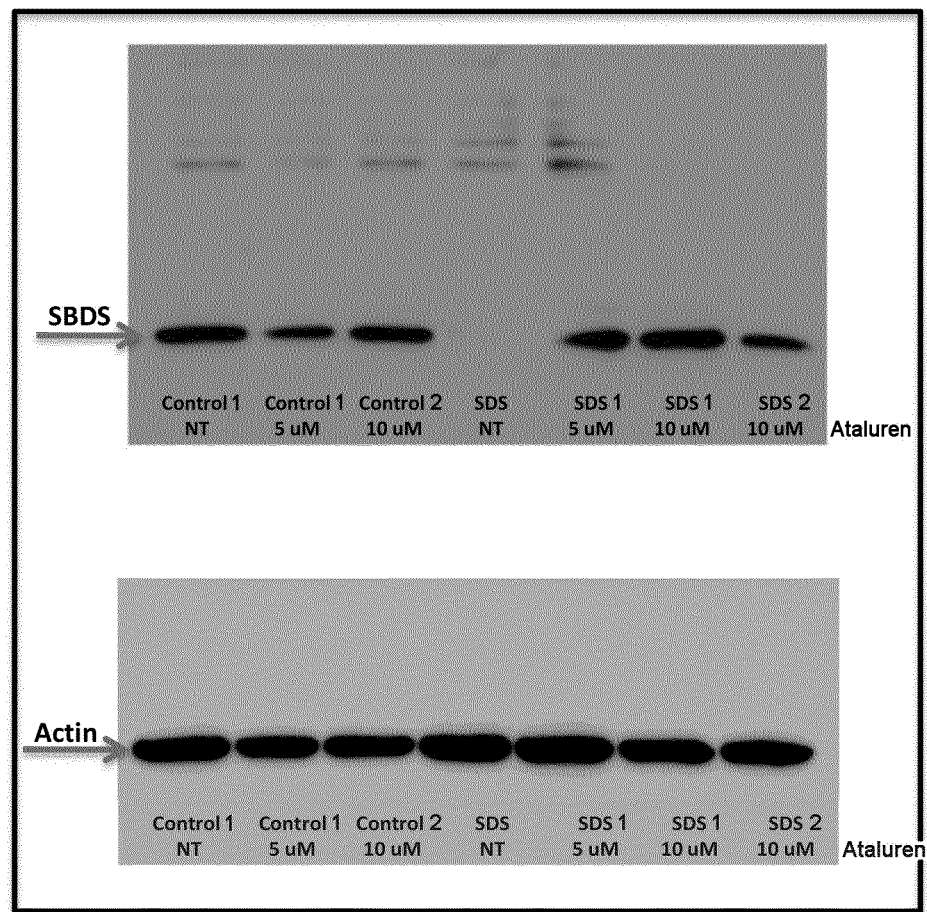

FIG. 2. Effect of Ataluren on SBDS protein expression in LCLs. SBDS protein expression after 24 hours exposure to the indicated dose of Ataluren.

Figure 3:
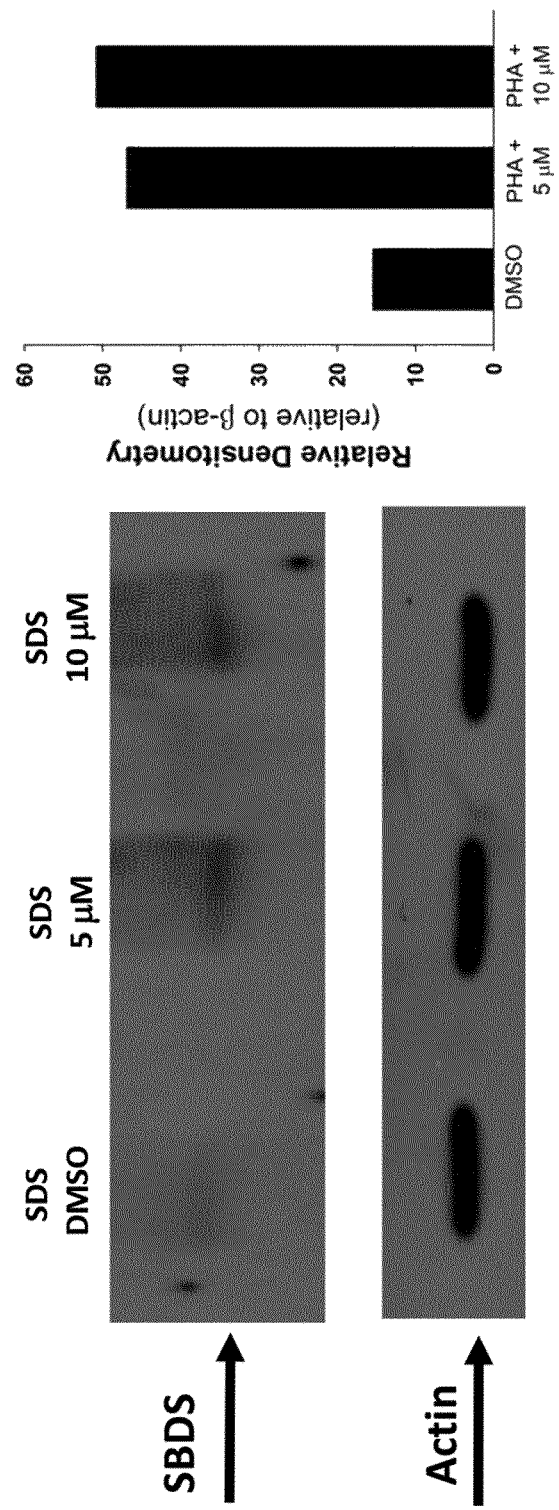

FIG. 3. Ataluren restores SBDS protein expression in peripheral blood mononuclear cells. PBMCs were freshly isolated from whole blood sample of a patient carrying 183-184TA>TC nonsense mutation, then incubated for 72 hours in PHA supplemented medium in the absence (DMSO) or in the presence of 5, 10 μM Ataluren. Cell lysates were collected and Western blot analyses was performed. Densitometry analysis is shown on the right panel.

Figure 4:
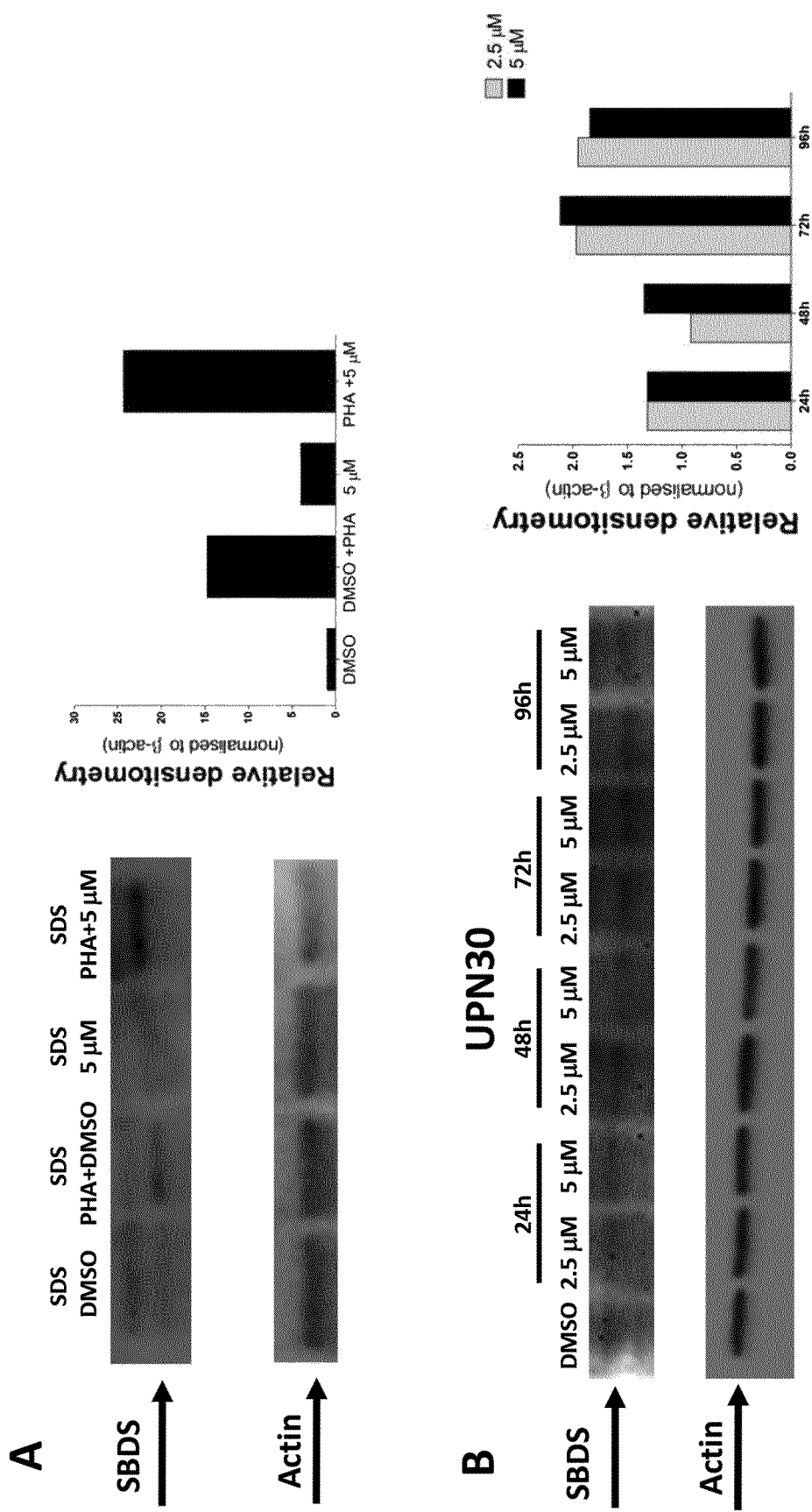

FIG. 4. Ataluren restores SBDS protein expression in bone marrow stem cells. A. Bone marrow hematopoietic progenitors were incubated in the presence or in the absence (DMSO) of 5 μM Ataluren for 72 hours in medium containing PHA (Phytohemagglutinin). B. Bone marrow Mesenchymal Stromal Cells (MSCs) were freshly isolated from bone marrow biopsy and incubated with 2.5, 5 μM Ataluren for a lapse of time ranging from 24 to 96 hours. Densitometry analysis is shown on the right panels.

Figure 5:
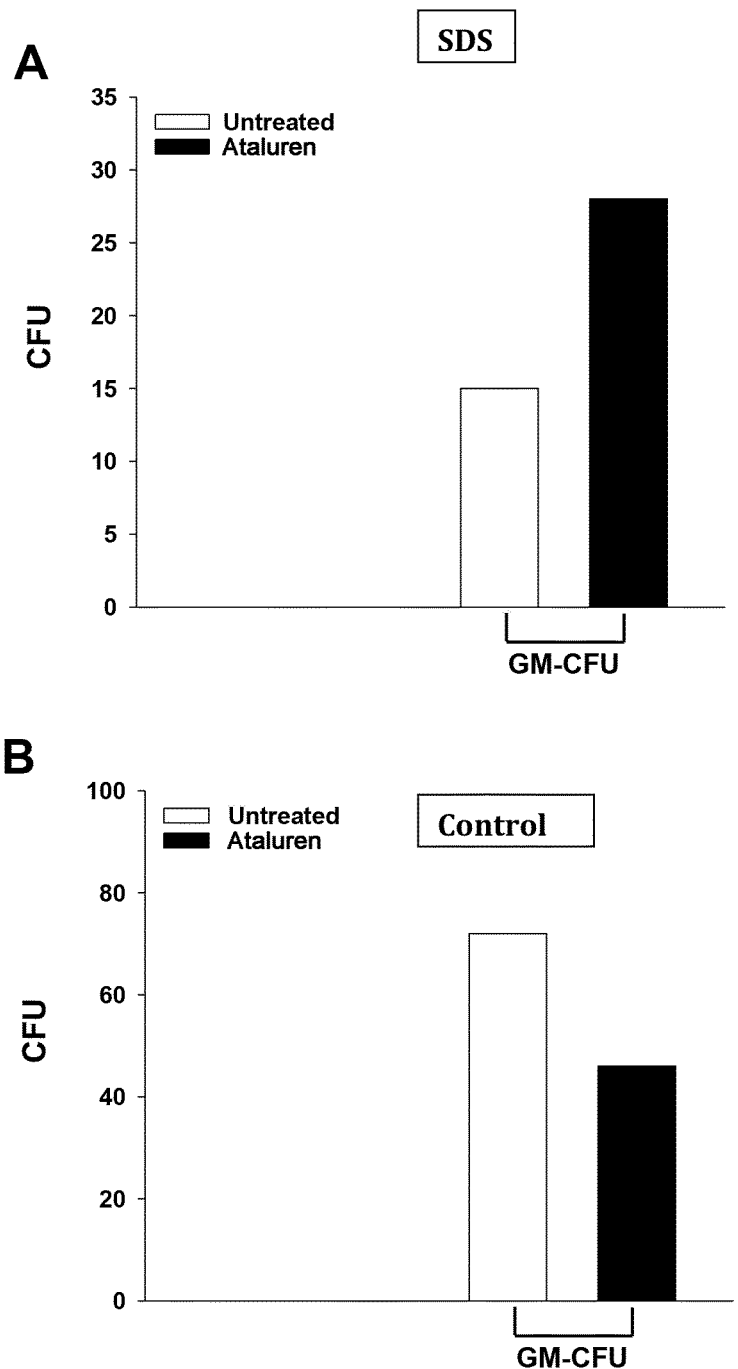

FIG. 5. Ataluren increases myeloid progenitor proliferation in SDS patients. Colony-forming units (CFU) of myeloid lineage (GM-CFU) were counted at the end of the assay.

Figure 6:
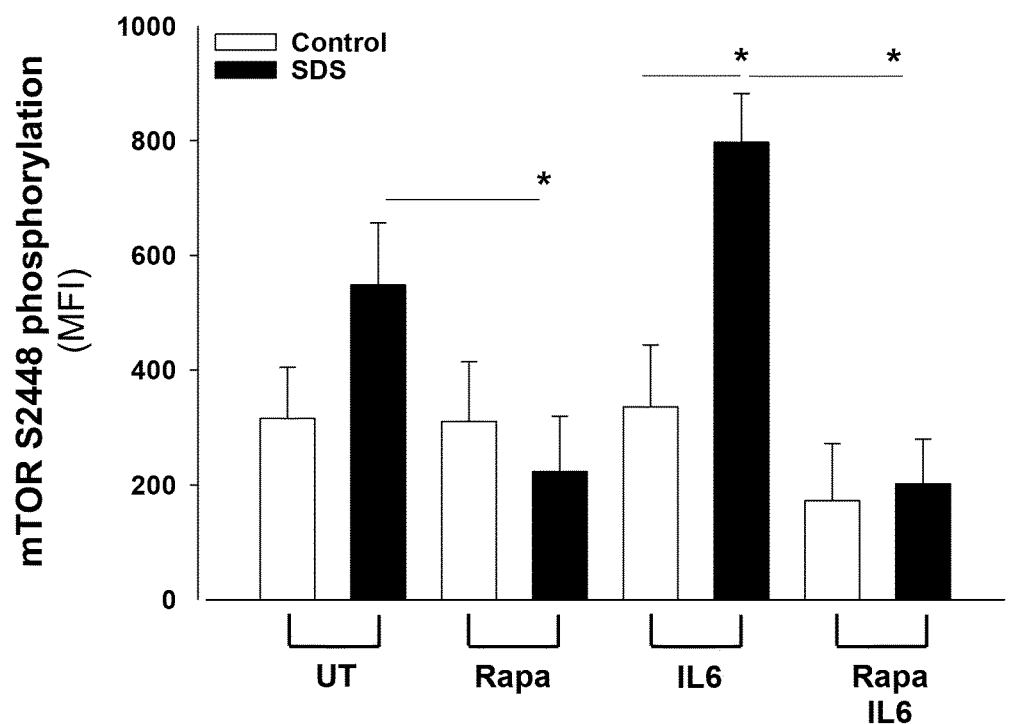

FIG. 6. Hyper-phosphorylation of mTOR (S2448) observed in SDS patients. LCLs derived from healthy donor subjects (white bars) or from SDS patients carrying the 258+2T>C, 183-184TA>CT genotype (black bars) were pre-incubated in the presence or in the absence (UT) of 350 nM Rapamycin for 1 hour and subsequently stimulated with 10 ng/ml of human recombinant IL-6 for further 15 mins. Data are mean±SEM of three independent experiments in duplicate. (*) Student's t-test p<0.05.

Figure 7:
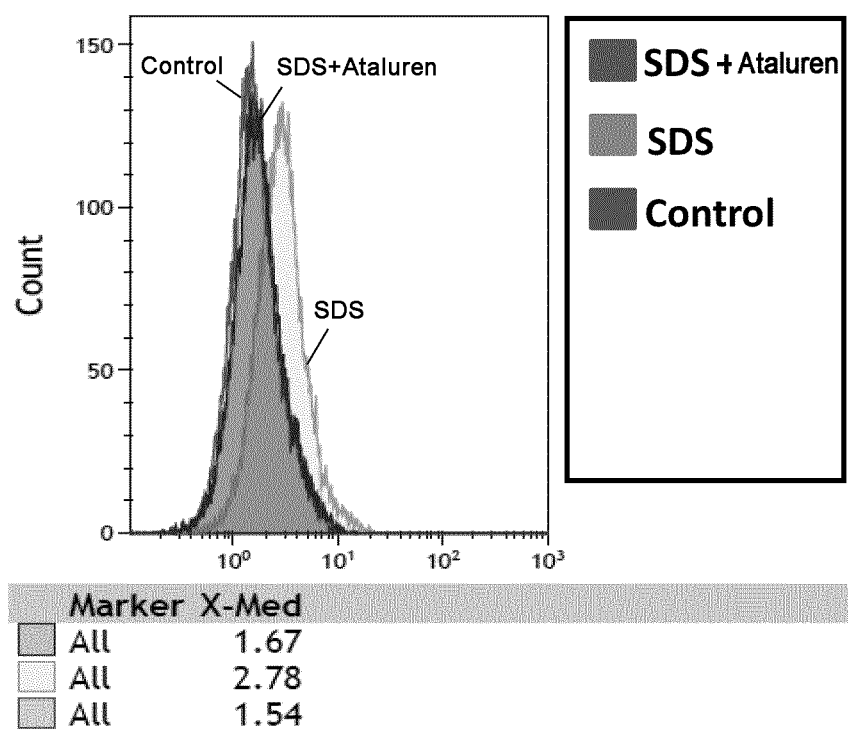

FIG. 7. Ataluren reduces mTOR hyper-phosphorylation (S2448) in SDS LCLs. LCLs derived from SDS patient carrying 258+2T>C and 183-184TA>CT genotype were pre-incubated in the presence (Ataluren) or in the absence of 5 μM Ataluren for 24 hours. Phosphorylation of Serine 2448 residue of mTOR was detected by flow cytometry assay as described in the methods section. Histogram medians (X-Med) are reported below the graph.

Figure 8:
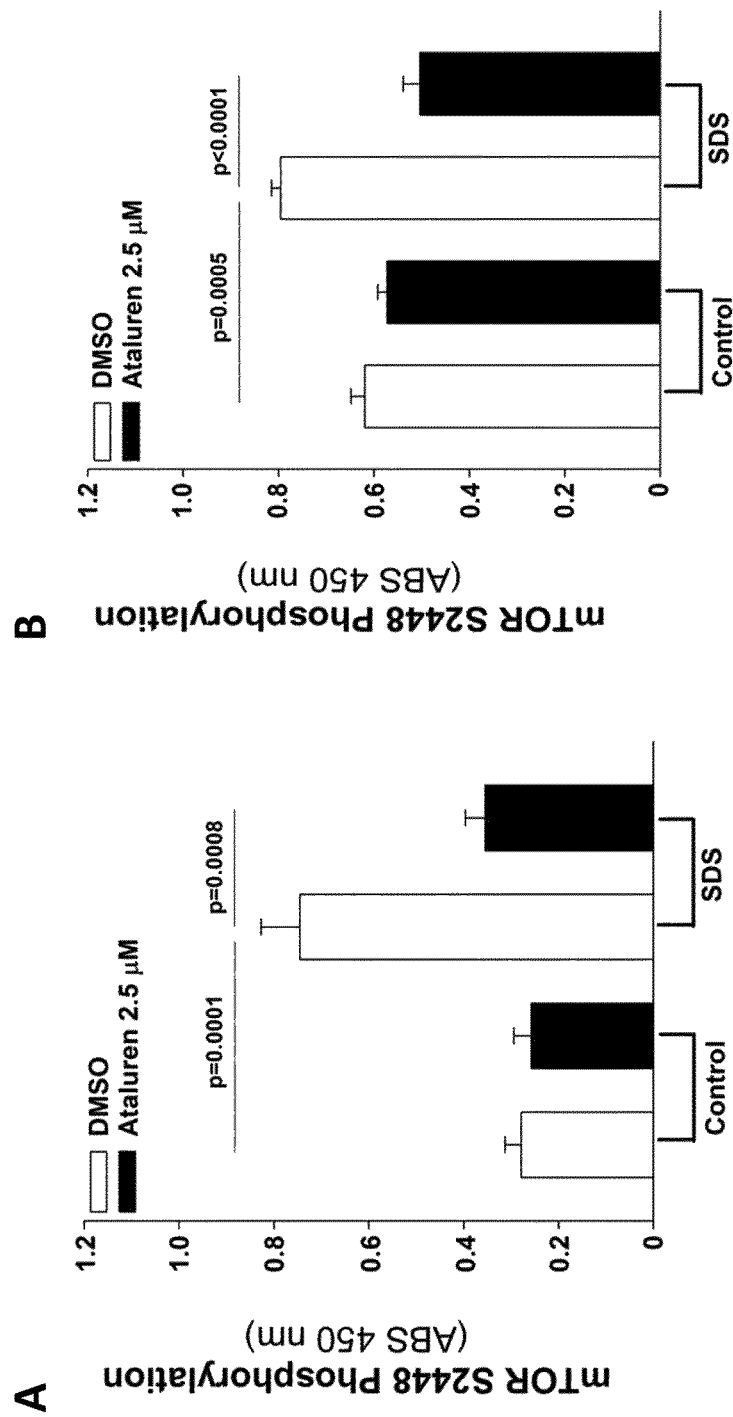

FIG. 8. Ataluren reduces mTOR phosphorylation in bone marrow mesenchymal stromal cells. Cells were incubated in the presence or absence of 2.5 μM Ataluren for 72 hours. mTOR (S2448) phosphorylation was quantified by ELISA. A. LCLs. B. MSCs. Data are mean±SEM of five LCLs/MSCs obtained from different SDS patients carrying nonsense mutations and compared to five healthy control samples. Experiments were performed in duplicate. Differences between SDS-DMSO and SDS-Ataluren groups were found after conduction of paired t-tests.

DESCRIPTION

Object of the present invention is a compound of formula (I)

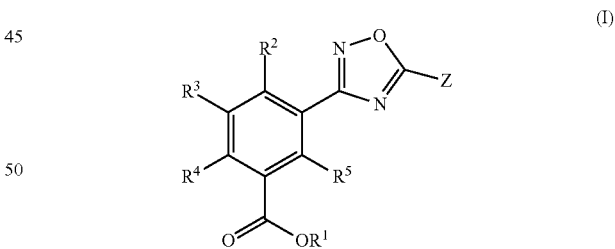

wherein Z is substituted or unsubstituted aryl, substituted or unsubstituted heteroaryl, substituted or unsubstituted cycloalkyl, substituted or unsubstituted alkyl, substituted or unsubstituted alkenyl, substituted or unsubstituted heterocycle, substituted or unsubstituted arylalkyl;

$R^1$ is hydrogen, substituted or unsubstituted alkyl, substituted or unsubstituted cycloalkyl, substituted or unsubstituted heterocycloalkyl, substituted or unsubstituted aryl, substituted or unsubstituted heteroaryl, —(CH$_2$CH$_2$)$_n$OR$^6$ or any biohydrolyzable group;

$R^2$, $R^3$, $R^4$, $R^5$ and $R^6$ are independently hydrogen, substituted or unsubstituted alkyl, substituted or unsubstituted alkenyl, substituted or unsubstituted alkynyl; substituted or unsubstituted cycloalkyl, substituted or unsubstituted heterocycloalkyl, substituted or unsubstituted aryl, substituted or unsubstituted heteroaryl, alkoxy, aryloxy, heteroaryloxy, halogen, $CF_3$, $OCF_3$, $OCHF_2$, CN, COOH, $COOR^7$, $SO_2R^7$, $NO_2$, $NH_2$, or $N(R^7)_2$;

each occurrence of $R^7$ is independently hydrogen, substituted or unsubstituted alkyl, substituted or unsubstituted alkenyl, substituted or unsubstituted alkynyl; substituted or unsubstituted cycloalkyl, substituted or unsubstituted heterocycloalkyl, substituted or unsubstituted aryl, substituted or unsubstituted heteroaryl, alkoxy, aryloxy, heteroaryloxy, halogen or $CF_3$;

n is an integer from 1 to 7 for use in the treatment of a ribosomopathy.

In a preferred embodiment, it is here described a compound of formula (II)

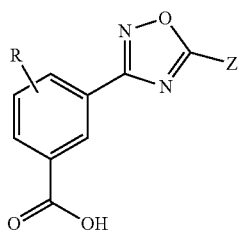

(II)

wherein Z is defined as in formula I and R is hydrogen or halogen, for use in the treatment of a ribosomopathy.

In a still more preferred embodiment, said compound is a compound of formula II, wherein Z is substituted or unsubstituted aryl, and R is hydrogen or halogen, for use in the treatment of a ribosomopathy.

Preferably said ribosomopathy is characterized by at least one of: bone marrow failure, hematological impairment, developmental abnormalities and increased risk of cancer. Preferably, said ribosomopathy is selected from the group consisting of: Shwachman-Diamond Syndrome (SDS), Diamond-Blackfan Anemia (DBA), X-linked dyskeratosiscongenita (DKC) and Treacher Collins syndrome (TCS); most preferably said ribosomopathy is SDS. More preferably, said compound is Ataluren

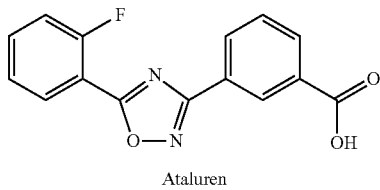 [SMILES: O=C(O)c1cccc(-c2noc(-c3ccccc3F)n2)c1]

Ataluren

In a preferred embodiment of the invention, the compounds of formulas I and II are pharmaceutically acceptable salts, hydrates, clathrates, prodrugs, polymorphs, bio-hydrolyzable esters, racemates, or purified stereoisomers including, but not limited to, optically pure enantiomers and diastereomers.

In a further embodiment, it is here described a method of treatment of a ribosomopathy comprising administering a therapeutically effective amount of a compound of formula (I) or of formula (II) as described above.

As used herein, a "therapeutically effective amount" refers to that amount of the compound of the invention sufficient to provide a therapeutic benefit in the treatment or management of the disease or to delay or minimize symptoms associated with the disease. Further, a therapeutically effective amount with respect to a compound of the invention means that amount of therapeutic agent alone, or in combination with other therapies, that provides a therapeutic benefit in the treatment or management of the disease. Used in connection with an amount of a compound of the invention, the term can encompass an amount that improves overall therapy, reduces or avoids symptoms or causes of disease, or enhances the therapeutic efficacy of or synergies with another therapeutic agent.

As used herein, unless otherwise specified, the term "substituted" means a group substituted by one to four or more substituents, such as, halo, trifluoromethyl, trifluoromethoxy, hydroxy, alkoxy, cycloalkyoxy, heterocylooxy, oxo, alkanoyl, alkylcarbonyl, cycloalkyl, aryl, aryloxy, aralkyl, alkanoyloxy, cyano, azido, amino, alkylamino, arylamino, aralkylamino, cycloalkylamino, heterocycloamino, mono and disubstituted amino in which the two substituents on the amino group are selected from alkyl, aryl, aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e. g., SO2NH2), substituted sulfonamido, nitro, carboxy, carbamyl (e. g. CONH2), substituted carbamyl (e. g., CONH alkyl, CONH aryl, CONH aralkyl or instances where there are two substituents on the nitrogen selected from alkyl, aryl or aralkyl), alkoxycarbonyl, aryl, substituted aryl, guanidino and heterocyclo, such as, indolyl, imidazolyl, furyl, thienyl, thiazolyl, pyrrolidyl, pyridyl, pyrimidyl and the like. Wherein, as noted above, the substituents themselves are further substituted, such further substituents are selected from the group consisting of halogen, alkyl, alkoxy, aryl and aralkyl. In a particular embodiment, the term substituted does not mean cyano.

As used herein, unless otherwise specified, the term "alkyl" means a saturated straight chain or branched non-cyclic hydrocarbon having from 1 to 20 carbon atoms, most preferably 1 to 4 carbon atoms.

Representative saturated straight chain alkyls include-methyl, -ethyl, -n-propyl, -n-butyl, -n-pentyl, -n-hexyl, -n-heptyl, -n-octyl, -n-nonyl and -n-decyl; while saturated branched alkyls include—isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimetliylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. An alkyl group can be unsubstituted or substituted. Unsaturated alkyl groups include alkenyl groups and alkynyl groups, which are discussed below.

As used herein, unless otherwise specified the term "alkenyl group" means a straight chain or branched non-cyclic hydrocarbon having from 2 to 20 carbon atoms, more preferably 2-10 carbon atoms, most preferably 2-6 carbon atoms, and including at least one carbon-carbon double bond. Representative straight chain and branched (C2-Clo)

alkenyls include-vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1octenyl, -2-octenyl, -3-octenyl, -1-nonenyl, -2-nonenyl, -3-nonenyl, -1decenyl, -2-decenyl, -3-decenyl and the like. The double bond of an alkenyl group can be unconjugated or conjugated to another unsaturated group. An alkenyl group can be unsubstituted or substituted. As used herein, unless otherwise specified the term "alkynyl group" means a straight chain or branched non-cyclic hydrocarbon having from 2 to 20 carbon atoms, more preferably 2-10 carbon atoms, most preferably 2-6 carbon atoms, and including at least one carbon-carbon triple bond. Representative straight chain and branched-(C2-Clo) alkynyls include-acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl, and the like. The triple bond of an alkynyl group can be unconjugated or conjugated to another unsaturated group. An alkynyl group can be unsubstituted or substituted.

As used herein, unless otherwise specified the term "halogen" or "halo" means fluorine, chlorine, bromine, or iodine. Unless otherwise specified the term "alkyl sulfonyl" means -Alkyl-$SO_3H$ or —$SO_3$-alkyl, wherein alkyl is defined as above, including-$SO_2$—$CH_3$, —$SO_2$—$CH_2CH_3$, —$SO_2$—$(CH_2)_2CH_3$, —$SO_2$—$(CH_2)_3CH_3$, —$SO_2$—$(CH_2)_4CH_3$, —$SO_2$—$(CH_2)_5CH_3$, and the like.

As used herein, unless otherwise specified the term "carboxyl" and "carboxy" mean —COOH.

As used herein, unless otherwise specified the term "alkoxy" means-O-(alkyl), wherein alkyl is defined above, including-$OCH_3$, —$OCH_2CH_3$, —$O(CH_2)_2CH_3$, —$O(CH_2)_3CH_3$, —$O(CH_2)_4CH_3$, —$O(CH_2)_5CH_3$, and the like.

As used herein, unless otherwise specified the term "alkoxycarbonyl" means —C(=O)O-(alkyl), wherein alkyl is defined above, including —C(=O)O—$CH_3$, —C(=O)O—$CH_2CH_3$, —C(=O) O—$(CH_2)_2CH_3$, —C(=O)O—$(CH_2)_3CH_3$, —C(=O)O—$(CH_2)_4CH_3$, —C(=O)O—$(CH_2)_5CH_3$, and the like. In a preferred embodiment, the esters are biohydrolyzable (i.e., the ester is hydrolyzed to a carboxylic acid in vitro or in vivo). As used herein, unless otherwise specified the term "alkoxyalkyl" means -(alkyl)-O-(alkyl), wherein each "alkyl" is independently an alkyl group as defined above, including-$CH_2OCH_3$, —$CH_2OCH_2CH_3$, —$(CH_2)_2OCH_2CH_3$, —$(CH_2)_2O(CH_2)_2CH_3$, and the like.

As used herein, unless otherwise specified the term "aryl" means a carbocyclic aromatic ring containing from 5 to 14 ring atoms. The ring atoms of a carbocyclic aryl group are all carbon atoms. Aryl ring structures include compounds having one or more ring structures such as mono-, bi-, or tricyclic compounds as well as benzo-fused carbocyclic moieties such as 5, 6, 7, 8-tetrahydronaphthyl and the like. Preferably, the aryl group is a monocyclic ring or bicyclic ring. Representative aryl groups include phenyl, tolyl, anthracenyl, fluorenyl, indenyl, azulenyl, phenanthrenyl and naphthyl. A carbocyclic aryl group can be unsubstituted or substituted.

As used herein, unless otherwise specified the term "heteroaryl" means a carbocyclic aromatic ring containing from 5 to 14 ring atoms and the ring atoms contain at least one heteroatom, preferably 1 to 3 heteroatoms, independently selected from nitrogen, oxygen, or sulfur. Heteroaryl ring structures include compounds having one or more ring structures such as mono-, bi-, or tricyclic compounds as well as fused heterocycle moieties. Representative heteroaryls are triazolyl, tetrazolyl, oxadiazolyl, pyridyl, furyl, benzofuranyl, thiophenyl, benzothiophenyl, benzoisoxazolyl, benzoisothiazolyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pylidazinyl, pyrimidinyl, pyrazinyl, triazinyl, cinnolinyl, phthalazinyl, quinazolinyl, benzoquinazolinyl, acridinyl, pyrimidyl and oxazolyl. A group can be unsubstituted or substituted.

Unless otherwise specified the term "aryloxy" means-O-aryl group, wherein aryl is as defined above. An aryloxy group can be unsubstituted or substituted.

As used herein, unless otherwise specified the term "arylalkyl" means -(alkyl)-(aryl), wherein alkyl and aryl are defined above, including, but not limited to —$(CH_2)$phenyl, —$(CH_2)_2$phenyl, —$(CH_2)_3$phenyl, —CH$(phenyl)_2$, —CH$(phenyl)_3$, —$(CH_2)$tolyl, —$(CH_2)$alathracenyl, —$(CH_2)$fluorenyl, —$(CH_2)$indenyl, —$(CH_2)$azulenyl, —$(CH_2)$naphthyl, and the like.

As used herein, unless otherwise specified the term "heteroarylalkyl" means -(alkyl)-(heteroaryl), wherein alkyl and heteroaryl are defined above, including, but not limited to —$(CH_2)$ Pyridyl, —$(CH_2)_2$pyridyl, —$(CH_2)_3$pyridyl, —CH$(pyridyl)_2$, —C$(pyridyl)_3$, —$(CH_2)$triazolyl, —$(CH_2)$tetrazolyl, —$(CH_2)$oxadiazolyl, —$(CH_2)$furyl, —$(CH_2)$benzofuranyl, —$(CH_2)$thiophenyl, —$(CH_2)$benzothiophenyl, and the like.

As used herein, unless otherwise specified the term "arylalkyloxy" means —O-(alkyl)-(aryl), wherein alkyl and aryl are defined above, including, but not limited to —O—$(CH_2)_2$phenyl, —O—$(CH_2)_3$phenyl, —O—CH$(phenyl)_2$, —O—CH$(phenyl)_3$, —O—$(CH_2)$tolyl, —O—$(CH_2)$anthracenyl, —O—$(CH_2)$ fluorenyl, —O—$(CH_2)$ indenyl, —O—$(CH_2)$ azulenyl, —O—$(CH_2)$naphthyl, and the like.

As used herein, unless otherwise specified the term "cycloalkyl" means a monocyclic or polycyclic saturated ring comprising carbon and hydrogen atoms and having no carbon-carbon multiple bonds. A cycloalkyl group can be unsubstituted or substituted.

Examples of cycloalkyl groups include, but are not limited to, (C3-C7)cycloalkyl groups, including cyclopropyl, cyclobutyl, cyclopentyl, cyclohexyl, and cycloheptyl, and saturated cyclic and bicyclic terpenes. A cycloalkyl group can be unsubstituted or substituted. Preferably, the cycloalkyl group is a monocyclic ring or bicyclic ring.

As used herein, unless otherwise specified the term "heterocyclyl" means a monocyclic or polycyclic ring comprising carbon and hydrogen atoms, optionally having 1 to 4 multiple bonds, and the ring atoms contain at least one heteroatom, preferably 1 to 3 heteroatoms, independently selected from nitrogen, oxygen, and sulfur. Heterocyclyl ring structures include compounds having one or more ring structures such as mono-, bi-, or tricylic compounds. Preferably, the heterocyclyl group is a monocyclic ring or bicyclic ring. Representative heterocycles include, but are not limited to morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, and the like. A heterocyclyl ring can be unsubstituted or substituted.

Unless otherwise specified the term "cycloalkyloxy" means —O-(cycloalkyl), wherein cycloalkyl is defined above.

As used herein, unless otherwise specified the term "cycloalkylalkyloxy" means —O-(alkyl)-(cycloalkyl), wherein cycloalkyl and alkyl are defined above, including, but not limited to —O-cyclopropyl, —O-cyclobutyl, —O-cyclopentyl, —O-cyclohexyl, —O-cycloheptyl and the like.

As used herein, unless otherwise specified the term "aminoalkoxy" means —O-(alkyl)-$NH_2$, wherein alkyl is defined above, including, but not limited to —O—$CH_2$—$NH_2$, —O—$(CH_2)_2$—$NH_2$, —O—$(CH_2)_3$—$NH_2$, —O—$(CH_2)_4$—$NH_2$, —O—$(CH_2)_5$—$NH_2$, and the like.

As used herein, unless otherwise specified the term "alkylamino" means —NH(alkyl) or —N(alkyl) (alkyl), wherein alkyl is defined above, including, but not limited to $NHCH_3$, —$NHCH_2CH_3$, —$NH(CH_2)_2CH_3$, —$NH((CH_2)_3CH_3$, —$NH(CH_2)_4CH_3$, —$NH(CH_2)_5CH_3$, —$N(CH_3)_2$, —$N(CH_2CH_3)_2$, —$N((CH_2)_2CH_3)_2$, —$N(CH_3)$ $(CH_2CH_3)$, and the like.

As used herein, unless otherwise specified the term "arylamino" means-NH(aryl), wherein aryl is defined above, including, but not limited to —NH(phenyl), —NH(tolyl), —NH(anthracenyl), —NH(fluorenyl), —NH(indenyl), —NH(azulenyl), —NH pyridinyl), —NH (naphthyl), and the like.

As used herein, unless otherwise specified the term "arylalkylamino" means-NH-(alkyl)-(aryl), wherein alkyl and aryl are defined above, including-NH—$CH_2$-(phenyl), —NH—$CH_2$-(tolyl), —NH—$CH_2$-(anthracenyl), —NH—$CH_2$-(fluorenyl), —NH—$CH_2$-(indenyl), —NH—$CH_2$-(azulenyl), —NH—$CH_2$-(pyridinyl), —NH—$CH_2$-(naphthyl), —NH—$(CH_2)_2$-(phenyl) and the like.

As used herein, unless otherwise specified the term "cycloalkylamino" means —NH-(cycloalkyl), wherein cycloalkyl is defined above, including-NH-cyclopropyl, —NH-cyclobutyl, —NH-cyclopentyl, —NH-cyclohexyl, —NH-cycloheptyl, and the like.

As used herein, unless otherwise specified the term "aminoalkyl" means -(alkyl)-$NH_2$, wherein alkyl is defined above, including-$CH_2$—$NH_2$, —$(CH_2)_2$—$NH_2$, —$(CH_2)_3$—$NH_2$, —$(CH_2)_4$—$NH_2$, —$(CH_2)_5$—$NH_2$ and the like.

As used herein, unless otherwise specified the term "alkylaminoalkyl" means-(alkyl)-NH (alkyl) or -(alkyl)-N (alkyl) (alkyl), wherein each "alkyl" is independently an alkyl group defined above, including-$CH_2$—NH—$CH_3$, —$CH_2$—$NHCH_2CH_3$, —$CH_2$—$NH(CH_2)_2CH_3$, —$CH_2$—NH $(CH_2)_3CH_3$, —$CH_2$—$NH(CH_2)_4CH_3$, —$CH_2$—NH $(CH_2)_5CH_3$, —$(CH_2)_2$—NH—$CH_3$, —$CH_2$—$N(CH)_2$, —$CH_2$—$N(CH_2CH_3)_2$, —$CH_2$—$N((CH_2)_2CH_3)_2$, —$CH_2$—$N(CH_3)$ $(CH_2CH_3)$, —$(CH_2)_2$—$N(CH_3)_2$, and the like.

As used herein, the term "pharmaceutically acceptable salts" refer to salts prepared from pharmaceutically acceptable non-toxic acids or bases including inorganic acids and bases and organic acids and bases. Suitable pharmaceutically acceptable base addition salts for the compound of the present invention include, but are not limited to, metallic salts made from aluminum, calcium, lithium, magnesium, potassium, sodium and zinc or organic salts made from lysine, N, N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids.

Pharmaceutical compositions and single unit dosage forms comprising a compound according to the invention, or a pharmaceutically acceptable polymorph, prodrug, salt, solvate, hydrate, or clathrate thereof, are also encompassed by the invention for use in the treatment of a ribosomopathy.

Individual dosage forms of the invention may be suitable for oral, mucosal (including sublingual, buccal, rectal, nasal, or vaginal), parenteral (including subcutaneous, intramuscular, bolus injection, intra-arterial, or intravenous), transdermal, or topical administration.

Pharmaceutical compositions and dosage forms of the invention typically also comprise one or more pharmaceutically acceptable excipients. Preferably, pharmaceutical compositions according to the invention comprise the compounds of the invention, as described herein, as the sole active agent.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e. g., nasal sprays or inhalers); gels; liquid dosage forms suitable for oral or mucosal administration to a patient, including suspensions (e. g., aqueous or non-aqueous liquid suspensions, oil-in-water emulsions, or a water-in-oil liquid emulsions), solutions, and elixirs; liquid dosage forms suitable for parenteral administration to a patient; and sterile solids (e. g., crystalline or amorphous solids) that can be reconstituted to provide liquid dosage forms suitable for parenteral administration to a patient.

The composition, shape, and type of dosage forms of the invention will typically vary depending on their use. Typical dosage forms of the invention, comprising a compound of the invention, or a pharmaceutically acceptable salt, solvate, clathrate, hydrate, polymorph or prodrug thereof, lie within the range of from about 0.1 mg to about 2000 mg per day, given as a single once-a-day dose in the morning but preferably as divided doses throughout the day taken with food.

Preferably, the daily dose is administered twice daily in equally divided doses. Specifically, a daily dose range should be from about 5 mg to about 500 mg per day, more specifically, between about 10 mg and about 200 mg per day. In managing the patient, the therapy should be initiated at a lower dose, perhaps about 1 mg to about 25 mg, and increased if necessary up to about 200 mg to about 2000 mg per day as either a single dose or divided doses, depending on the patient's global response.

Experimental Section

Methods

Cell Cultures

Generation of Lymphoblastoid cell lines (LCLs). B cells obtained from two healthy donor subjects (CTL 1 and 2) and three SDS patients (SDS 1, 2 and 3), all carrying 258+2T>C, 183-184TA>CT genotype, were isolated from peripheral blood by Rosette Sep B Lymphocyte Kit (Miltenyi Biotech, Bergisch Gladbach, Germany). B cell purity was verified by flow cytometry evaluating the expression of CD45 (common leucocytes antigen), CD19 (pan B lymphocytes) and by the exclusion of the expression of CD4, which is commonly expressed on T4 lymphocyte (bright fluorescence intensity) and monocytes (dim fluorescence intensity) and CD8 molecules expressed on T8 lymphocytes (bright fluorescence intensity) and NK cells (dim fluorescence intensity). B cells were seeded at a density of $3\times10^6$ cells in 12-well cell culture plates in 3 ml RPMI-1640 medium (Life Technologies, Carlsbad, Calif.), supplemented with 1% glutamine and 10% fetal bovine serum (FBS) (Life Technologies) and infected for 18 hours with EBV derived from marmoset blood leukocytes B95.8 virus-producer cell lines as previously described[14]. Highly purified (99.5%) Peripheral Blood Mononuclear Cells (PBMCs) were isolated under LPS-free conditions from healthy donors or SDS patients by centrifugation on a Ficoll Hypaque gradient, as previously described[5].

Colony-Forming Unit Assay

SDS patients underwent bone marrow aspiration and biopsy from the posterior superior iliac crest following sedation. Bone marrow aspirates collected in preservative-free heparin underwent Percoll fractionation. Light-density mononuclear cells underwent $CD34^+$ enrichment by the Mini-MACS immunomagnetic separation system (MiltenyiBiotec, Auburn, Calif., USA). $CD34^+$ cells were plated in duplicate at a density of $3\times10^3$ cells/ml in culture wells containing methylcellulose (Fluka, Buchs, Switzerland), 40 U/mL interleukin-3 (Immunex, Seattle, Wash., USA), 10 ng/mL granulocyte colony-stimulating factor (G-CSF; Amgen, Thousand Oaks, Calif., USA), 50 ng/mL mast cell growth factor (Immunex), and 2 U/mL erythropoietin (Ortho Biologics, Manati, PR). Cultures were incubated for 28 days, then scored for colony formation: granulocyte-macrophage colony-forming units (CFU-GM).

Western Blot

LCLs, PBMCs, bone marrow CD34+ stem cells and MSCs were seeded at $2.5\times10^6$ cells in RPMI 1640 medium (Life Technologies) supplemented with 1% glutamine and 10% FBS (Life Technologies) and incubated at 37° C. in the presence or in the absence of 5-10 µM Ataluren (Selleck Chemicals, Houston, Tex.) for 24 hours. Cell proteins were extracted and separated on 11% SDS-PAGE, and electroblotted onto Immobilon P filters (Millipore, Billerica, Mass.) previously blocked with 5% BSA in TBST (0.05% Tween-20). The membranes were probed with: i) anti-human SBDS rabbit polyclonal IgG antibody (amino acids 1 and 250 of SBDS, Abcam, Cambridge, Mass., dilution 1:1500); ii) monoclonal anti-R-Actin clone AC-15 (Sigma-Aldrich, St Louis, Mo.; A5441, diluted 1:2000) in 1% BSA TBST. Membranes were incubated overnight at 4° C. and after washes, membranes were incubated with the secondary antibody, horseradish peroxidase-coupled anti-rabbit IgG (Sigma-Aldrich, dilution 1:15000), for 1 hour. Immunocomplexes were detected with ECL Plus Western Blotting detection system (Amersham Biosciences, Little Chalfont, UK).

Flow Cytometry

LCLs were seeded at $2.5\times10^5$ cells in 2 aliquots and incubated at 37° C. Cells were incubated in the presence or in the absence of 350 nM Rapamycin (Sigma-Aldrich) for 1 hour or 5 µM Ataluren (Selleck Chemicals, Houston, Tex.) for 24 hours. Rapamycin-treated cells were further stimulated with 10 ng/ml human recombinant IL-6 (Sigma-Aldrich) for 15 mins. LCLs were fixed in 2% paraformaldehyde and permeabilized in 100% ice-cold methanol, washed twice in flow buffer (PBS, pH 7.2, with 0.2% BSA and 0.09% sodium azide) as previously described[16] and then stained with anti-p-S2448-mTOR-PE or isotype control-PE for 30 minutes (antibodies were purchased by Becton-Dickinson Biosciences, Franklin Lakes, N.J.). Cells were washed and acquired on a 10 color, 3 laser (Blue Solid State Diode: 488 nm, 22 mW, Red Solid State Diode: 638 nm, 25 mW, Violet Solid State Diode: 405 nm, 40 mW), Navios flow cytometer (Beckman Coulter, Indianapolis, Ind.). All acquired data files were analyzed using the "Navios" or Kaluza software, version 1.3 (Beckman Coulter, Indianapolis, Ind.).

ELISA

Analysis of phospho-mTOR was also performed by using the PathScan PhosphomTOR (Ser2448) Sandwich ELISA Kit (Cell Signaling, Danvers, Mass.), following the manufacturer's protocol. Briefly, $2.5\times10^6$ LCLs or MSCs were seeded in culture plates containing RPMI-1640 medium supplemented with 0.5% FBS and incubated at 37° C. for 24 hours in order to reach cell growth synchronization. Then, cells were incubated in the presence/absence of 2.5 µM Ataluren for 72 hours. Cells were washed twice with PBS, lysed with Lysis Buffer containing 1 mM PMSF (Sigma-Aldrich, St Louis, Mo.) and Protease Inhibitor Cocktail Tablets (Roche). Protein extracts (25 mg/ml) were added to each well of ELISA plate, and incubated overnight at 4° C. 100 µl of anti-mTOR S2448 rabbit detection antibody were added to each well and incubated at 37° C. for 1 hour. Anti-rabbit IgG, HRP-linked antibody was then used to recognize the bound detection antibody. HRP substrate TMB was added to develop color. Results were collected as the absorbance for this developed color, proportional to the amount of mTOR phosphorylated at S2448 site.

Example 1: Ataluren Restores SBDS Protein Expression in LCLs and Bone Marrow Stem Cells Derived from SDS Patients Lymphoblasts are immature cells that typically differentiate to form mature lymphocytes. Epstein-Barr virus infection is able to transform mature B cells into lymphoblastoid cell lines that have been reported to proliferate and expand almost indefinitely. Somatic mutation rate in LCLs is very low, about 0.3%,[17] allowing to conclude that LCLs can be used to perform genetic and proteomic analysis. We obtained LCLs derived from three SDS patients, all carrying the most common mutations of SBDS gene, namely 258+2T>C, which is a missense mutation, together with 183-184TA>CT, which is a nonsense mutation, and cell lines from three healthy donors. The expression of SBDS protein has been tested in said lymphoblastoid cells by western blot analysis. The results obtained indicate that the 28.8 KDa SBDS protein was expressed in healthy control cell lines and undetectable in SDS cell lines (FIG. 1).

LCLs obtained from healthy donors and SDS patients were exposed to 5-10 µM Ataluren for 24 hours and the expression of SBDS protein was then evaluated. Results indicate a huge restoration of SBDS expression in LCLs obtained from SDS patients upon Ataluren treatment (SDS columns, FIG. 2). No effect was observed upon incubation of healthy donor-derived LCLs with Ataluren (Control columns, FIG. 2). Importantly, 2.5 and 5 µM Ataluren restore SBDS expression also in primary PBMCs obtained from SDS patients (FIG. 3). Ataluren effect was then tested on bone marrow CD34' stem cells and Mesenchymal stem cells (MSCs) derived from patients carrying the 258+2T>C, 183-184TA>CT genotype. Results indicate a strong restoration of SBDS protein expression upon incubation of CD34+ stem cells with 5 µM Ataluren for 24 hours (FIG. 4).

Example 2: Ataluren Stimulates Myeloid Lineage Proliferation in Bone Marrow Stem Cell Cultures A colony-forming unit assay using bone marrow CD34+ stem cells obtained from a SDS patient carrying 258+2T>C and 183-184TA>CT mutations has been performed. Results indicate that after 28 days of culture in the presence of 5 µM Ataluren, SDS myeloid progenitors (GM-CFU) almost doubled in number compared to untreated cells (FIG. 5A). On the contrary, no additional pro-proliferative effect was shown in healthy donor-derived bone marrow CD34+ stem cells incubated with 5 µM Ataluren (FIG. 5B).

Example 3: SDS Patients Show mTOR Hyper-Activation

SDS LCLs untreated (UT) cells show hyper activation of mTOR pathway, as reported in FIG. 6, first block. LCLs were incubated in the presence of the well-known mTOR inhibitor rapamycin for 24 hours (Rapa), then were stimulated with IL-6 (10 ng/ml) for further 15 mins (IL6), as it has been recently reported that IL-6 induces mTOR activation, in particular mTORC1 complex, in other cell models[18].

LCLs obtained from SDS patients show higher levels of mTOR phosphorylation in serine 2448 residue than healthy control cells, as measured by flow cytometry assay (FIG. 6, third block, IL6). Rapamycin is able to reduce this activation (FIG. 6, fourth block, Rapa IL6), suggesting that the pathway involves the rapamycin-sensible mTORC1.

Example 4: Ataluren Inhibits mTOR (S2448) Phosphorylation in SDS LCLs and Bone Marrow MSCs LCLs and MSCs cells were pre-incubated in the presence or in the absence of 2.5-5 µM Ataluren for 24 hours. Results indicate that Ataluren is able to strongly inhibit the mTOR increased phosphorylation observed in SDS, as the phosphorylation levels in the presence of the treatment in SDS cells overlap the levels observed in the control population (FIGS. 7-8).

The observed effect of Ataluren on mTOR phosphorylation is of particular relevance in supporting a role for Ataluren in the treatment of a ribosomopathy. These findings clearly indicate that Ataluren promotes growth ad differentiation of myeloid colonies ex vivo, wherein bone marrow from patients affected by SDS is characterized by a decreased frequency of CD34 cells, which in turn present reduced ability to form hematopoietic colonies in Vitro.

BIBLIOGRAPHY

1. Nakhoul, H. et al. Ribosomopathies: mechanisms of disease. *Clin Med Insights Blood Disord* 7:7-16. doi: 10.4137/CMBD.S16952. (2014).
2. Boocock, G. R. et al. Mutations in SBDS are associated with Shwachman-Diamond syndrome. *Nat Genet* 33, 97-101, doi:10.1038/ng1062 (2003).
3. Minelli, A. et al. Incidence of Shwachman-Diamond syndrome. *Pediatr Blood Cancer* 59, 1334-1335, doi: 10.1002/pbc.24260 (2012).
4. Ganapathi, K. A. et al. The human Shwachman-Diamond syndrome protein, SBDS, associates with ribosomal RNA. *Blood* 110, 1458-1465, doi:10.1182/blood-2007-02-075184 (2007).
5. Finch, A. J. et al. Uncoupling of GTP hydrolysis from eIF6 release on the ribosome causes Shwachman-Diamond syndrome. *Genes Dev* 25, 917-929, doi:10.1101/gad.623011 (2011).
6. Burwick, N., Shimamura, A. & Liu, J. M. Non-Diamond Blackfan anemia disorders of ribosome function: Shwachman Diamond syndrome and 5q-syndrome. *Semin Hematol* 48, 136-143, doi:10.1053/j.seminhematol.2011.01.002 (2011).
7. Cipolli, M. Shwachman-Diamond syndrome: clinical phenotypes. *Pancreatology* 1, 543-548, doi:10.1159/000055858 (2001).
8. Stepanovic, V., Wessels, D., Goldman, F. D., Geiger, J. & Soll, D. R. The chemotaxis defect of Shwachman-Diamond Syndrome leukocytes. *Cell Motil Cytoskeleton* 57, 158-174, doi:10.1002/cm.10164 (2004).
9. Donadieu, J. et al. Analysis of risk factors for myelodysplasias, leukemias and death from infection among patients with congenital neutropenia. Experience of the French Severe Chronic Neutropenia Study Group. *Haematologica* 90, 45-53 (2005).
10. Maserati, E. et al. Shwachman syndrome as mutator phenotype responsible for myeloid dysplasia/neoplasia through karyotype instability and chromosomes 7 and 20 anomalies. *Genes Chromosomes Cancer* 45, 375-382, doi:10.1002/gcc.20301 (2006).
11. Welch, E. M. et al. PTC124 targets genetic disorders caused by nonsense mutations. *Nature* 447, 87-91 (2007).
12. Karijolich, J. & Yu, Y. T. Therapeutic suppression of premature termination codons: mechanisms and clinical considerations (review). *Int J Mol Med* 34, 355-62, doi: 10.3892/ijmm.2014.1809 (2014).
13. Kerem, E. et al. Ataluren for the treatment of nonsense-mutation cystic fibrosis: a randomised, double-blind, placebo-controlled phase 3 trial. *Lancet Respir Med* 2, 539-47, doi: 10.1016/S2213-2600(14)70100-6 (2014).
14. Roncella, S. et al. Establishment of an EBV-positive lymphoblastoid cell line that grows as a lymphoma in nude mice and expresses membrane CD2 molecules. *Int J Cancer* 45, 299-307 (1990).
15. Cassatella, M. A., et al. Molecular basis of interferon-g and lipopolysaccharide enhancement of phagocyte respiratory burst capability: studies on the gene expression of several NADPH oxidase components. *J. Biol. Chem.* 265, 20241 (1990).
16. Redell, M. S. et al. FACS analysis of Stat3/5 signaling reveals sensitivity to G-CSF and IL-6 as a significant prognostic factor in pediatric AML: a Children's Oncology Group report. *Blood* 121, 1083-1093, doi:10.1182/blood-2012-04-421925 (2013).
17. Sie, L., Loong, S. & Tan, E. K. Utility of lymphoblastoid cell lines. *J Neurosci Res* 87, 1953-1959, doi:10.1002/jnr.22000 (2009).
18. Ruwanpura, S. M. et al. Therapeutic Targeting of the IL-6 Trans-signalling/mTORC1 Axis in Pulmonary Emphysema. *Am J Respir Crit Care Med.* doi: 10.1164/rccm.201512-2368OC [Epub ahead of print] (2016)

The invention claimed is:

1. A method for the treatment of Shwachman-Diamond Syndrome (SDS) in a subject in need thereof comprising administering to the subject a therapeutically effective amount of ataluren, having the formula:

2. A method for the treatment of SDS, wherein the method comprises administering a pharmaceutical composition comprising ataluren according to claim 1 and a pharmaceutically acceptable carrier to a subject in need thereof.

3. The method of claim 1, wherein the treatment of SDS with ataluren restores SBDS protein expression in Lymphoblastoid Cell Lines (LCLs) and bone marrow stem cells derived from a subject in need thereof, where the subject is an SDS patient.

4. The method of claim 1, wherein the treatment of SDS with ataluren inhibits mTOR phosphorylation in SDS LCLs and bone marrow mesenchymal stem cells (MSCs) derived from a subject in need thereof, where the subject is an SDS patient.

5. The method of claim 1, wherein the therapeutically effective amount of ataluren is selected from a range of from about 5 mg to about 500 mg per day or a range of from about 10 mg to about 200 mg per day, wherein the amount is given as a single dose or as divided doses.

6. The method of claim 1, wherein the therapeutically effective amount of ataluren is initiated at a lower dose in a range of from about 1 mg to about 25 mg per day, then increased up to a range of from about 200 mg to about 2000 mg per day, wherein the amount is given as a single dose or as divided doses.

7. The method of claim 2, wherein the pharmaceutical composition comprises an amount of ataluren in a range from about 0.1 mg to about 2000 mg per day, wherein the dose is given as a single once-a-day dose or as divided doses throughout the day.

8. The method of claim 5, wherein the single dose is given in the morning.

9. The method of claim 6, wherein the single dose is given in the morning.

10. The method of claim 7, wherein the single dose is given in the morning.

11. The method of claim 5, wherein the divided doses are each taken with food.

12. The method of claim 6, wherein the divided doses are each taken with food.

13. The method of claim 7, wherein the divided doses are each taken with food.

* * * * *